US00PP16840P2

(12) United States Plant Patent
Pieters

(10) Patent No.: US PP16,840 P2
(45) Date of Patent: Jul. 18, 2006

(54) *CHRYSANTHEMUM* PLANT NAMED 'GEDI THREE GEL'

(50) Latin Name: *Chrysanthemum morifolium*
Varietal Denomination: Gedi Three Gel

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 11/095,899

(22) Filed: Mar. 30, 2005

(51) Int. Cl.
*A01H 5/00* (2006.01)

(52) U.S. Cl. ..... Plt./289

(58) Field of Classification Search ..... Plt./289, Plt./295
See application file for complete search history.

(56) References Cited

U.S. PATENT DOCUMENTS

PP13,455 P2 1/2003 Pieters
PP13,797 P2 5/2003 Pieters

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct garden-type *Chrysanthemum* cultivar is disclosed, characterized by the presence of dark yellow ray florets, yellow disk florets, and a free branching, mounding growth habit. The plant naturally blooms in the first two weeks of September.

1 Drawing Sheet

Figure 1:
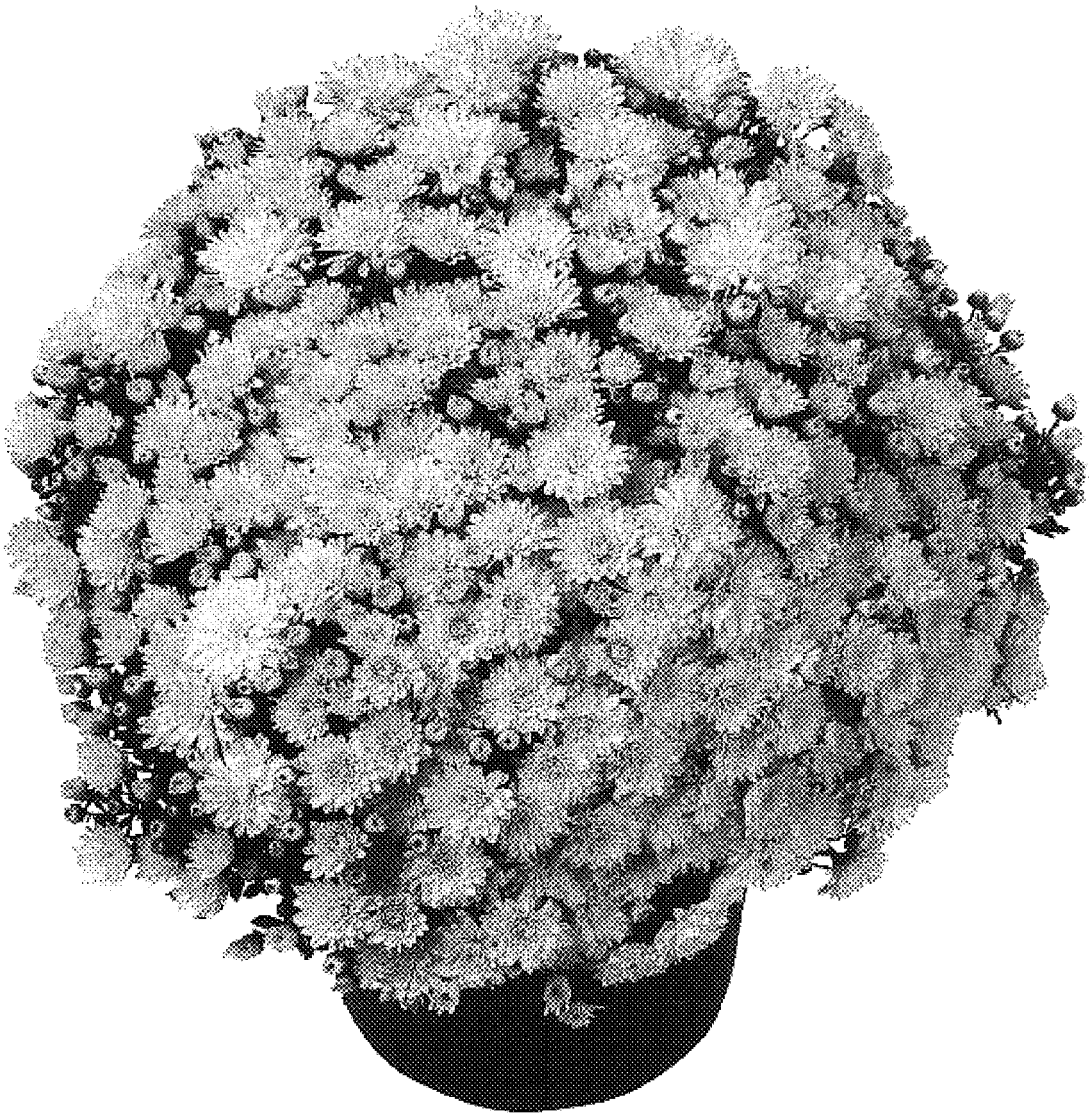

Latin name of the genus and species *Chrysanthemum morifolium.*
Variety denomination: 'Gedi Three Gel'.

BACKGROUND OF THE INVENTION

The new cultivar 'Gedi Three Gel' is a product of hybridization of a female parent *Chrysanthemum* plant '95 150 02' (undistributed, unpatented seedling) and a male parent *Chrysanthemum* plant variety 'Orka' (undistributed, unpatented in US). The new cultivar was discovered and selected by Dirk Pieters in Oostniewkerke, Belgium, in September, 1999.

Asexual reproduction of the new cultivar 'Gedi Three Gel' by terminal cuttings and tissue culture was performed in Oxnard, Calif. and has shown that the unique features of this cultivar are stable and reproduced true to type on successive generations.

SUMMARY OF THE INVENTION

The cultivar 'Gedi Three Gel' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Gel'. These characteristics in combination distinguish 'Gedi Three Gel' as a new and distinct *Chrysanthemum* cultivar:

1. Dark yellow ray florets.
2. Mounding growth habit.
3. Free branching habit.
4. Average vigor.
5. Naturally blooming beginning the first two weeks in September.

Plants of the new cultivar 'Gedi Three Gel' are similar to plants of the female parent '95 150 02' in most horticultural characteristics, however plants of the new cultivar have a darker yelow ray florets and a wider diameter flower than plants of the female parent variety. Further, the plants of the new cultivar 'Gedi Three Gel' have flowers that last approximately six days longer than the flowers of the female parent. The plants of the new cultivar 'Gedi Three Gel' are shorter than the plants of the female parent.

Plants of the new cultivar 'Gedi Three Gel' are similar to plants of the male parent variety, 'Orka,' in most horticultural characteristics, however plants of the new cultivar are shorter and have a smaller diameter flower than plants of the male parent variety. Additionally, plants of the new cultivar 'Gedi Three Gel' naturally bloom two weeks earlier than the male parent variety.

In comparison to the commercially available variety 'Gedi One Ces' (U.S. Plant Pat. No. 13,797) 'Gedi Thre Gel' has more flowers per flowering branch. Additionally, the new cultivar has a greater floral depth and less ray florets per flower than the comparable variety 'Gedi One Ces'.

In comparison to the commercially available variety 'Gedi One Avi' U.S. Plant Pat. No. 13,4550), the new variety has darker yellow ray florets and a larger floral diameter. Further, the new variety 'Gedi Three Gel' has about 10 more flowers per flowering branch than does the comparable variety 'Gedi One Avi'.

BRIEF DESCRIPTION OF THE PHOTOGRAPH

The accompanying photograph in FIG. 1 illustrates in full color a typical plant of 'Gedi Three Gel' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Gel' plants grown in a greenhouse in Oxnard, Calif., during the month of September, 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

PROPAGATION

Time to rooting: 7 to 14 days at approximately 21° C.
Root description: Fine, fibrous.

PLANT

Commercial classification: Garden *Chrysanthemum.*
Growth habit: Mounding herbaceous perennial.
Height: Approxiately 25.5 cm.
Plant spread: Approximately 28 cm.
Growth rate: Moderate.
Branching characteristics: Free branching.
Length of lateral branches: Approximately 20 cm.
Number of leaves per lateral branch: Approximately 17.
Age of plant described: Approximately 140 days from a rooted cutting.

FOLIAGE

Leaf:
- *Arrangement.*—Alternate.
- *Average length.*—Approximately 5.4 cm.
- *Average width.*—Approximately 4.8 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 2.6 cm.
- *Color.*—Young foliage upper side: Near Green 137A. Young foliage under side: Near Green 137B. Mature foliage upper side: Near Green 137A. Mature foliage under side: Near Green 138A.
- *Venation.*13 Type: Palmately net. Venation color upper side: Near Yellow-green 144C. Venation color under side: Near Green 138B.

Petiole:
- *Average length.*—Approximately 2.1 cm.
- *Color.*—Near Green 138A.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Form.*—Decorative.
- *Natural flowering season.*—Approximately the first two weeks of September.
- *Number of flowers per lateral branch.*—Approximately 22.
- *Diameter.*—Approximately 6.2 cm.
- *Depth.*—Approximately 3.1 cm.
- *Longevity on plant.*—Approximately 29 days.
- *Persistence.*—Persistent.

Ray florets:
- *Appearance.*—Matte.
- *Texture.*—Smooth.
- *Average number of ray florets per flower.*—Approximately 180.
- *Shape.*—Oblong.
- *Aspect.*—Flat.
- *Margin.*—Entire.
- *Apex.*—Retuse.
- *Length.*—Approximately 3.1 cm.
- *Width.*—Approximately 0.9 cm.
- *Color.*—Upper surface at first opening: Near Yellow-orange 15A. Upper surface at maturity: Near Yellow 13B. Upper surface at fading: Near Yellow 13C. Under surface at first opening: Near Yellow-orange 20A. Under surface at maturity: Near Yellow-orange 14B. Under surface at fading: Near Yellow 13C.

Disc florets:
- *Appearance.*—Shiny.
- *Texture.*—Smooth.
- *Average number of florets per disc.*—Approximately 20.
- *Shape.*—Cylindric.
- *Apex.*—Obtuse.
- *Average length.*—Approximately 0.4 cm.
- *Average width.*—Approximately 0.1 cm.
- *Color.* —At first opening: Near Yellow-green 154D. At maturity: Near Yellow 4C. At fading: Near Yellow-orange 16B.

Peduncle:
- *Length.*—At terminal end (shortest): Approximately 4.3 cm. At lateral end (longest): Approximately 6.5 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Lightly pubescent.

*Flower bud:*
- *Length.*—Approximately 1 cm.
- *Diameter.*—Approximately 0.9 cm.
- *Form.*—Globular.
- *Color.*—Near Yellow-orange 16A.

Involucral bracts (phyllaries):
- *Appearance.*—Matte.
- *Texture.*—Lightly pubescent.
- *Number.*—Approximately 54.
- *Shape.*—Oblanceolate.
- *Margin.*—Entire.
- *Apex.*—Acute.
- *Length.*—Approximately 1.1 cm.
- *Width.*—Approximately 0.8 cm.
- *Color.*—Upper side: Near Green 138A. Under side: Near Green 138A.

REPRODUCTIVE ORGANS

Ray florets:
- *Number of pistils per floret.*—1.
- *Stigma shape.*—2 branched.
- *Stigma color.*—Near Yellow 13A.
- *Style color.*—Near Yellow 2C.
- *Style length.*—Approximately 0.8 cm.
- *Stamens.*—Absent.

Disc florets:

*Number of pistils per floret.*—1.
*Stigma shape.*—Two-branched.
*Stigma color.*—Near Yellow 2C.
*Style length.*—Approximately 0.3 cm.
*Style color.*—Near Yellow-green 154D.
*Number of stamens per floret.*—Approximately 5.
*Anther shape.*—Tubular.
*Anther color.* —Near Yellow 13B.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperature about −2° C. Non-flowering plants are hardy in the approximate range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Gel' as herein illustrated and described.

* * * * *